United States Patent [19]

King

[11] 4,327,729
[45] May 4, 1982

[54] LOW-DENSITY DISPOSABLE ABSORBENT BANDAGE HAVING LOW STRETCH, WET STRENGTH CENTER PLY TO PROVIDE IMPROVED PAD INTEGRITY IN USE

[75] Inventor: Lawrence W. King, Cincinnati, Ohio

[73] Assignee: The Procter & Gamble Company, Cincinnati, Ohio

[21] Appl. No.: 810,661

[22] Filed: Jun. 27, 1977

[51] Int. Cl.³ .............................................. A61F 13/16
[52] U.S. Cl. ................................................ 128/287
[58] Field of Search ................... 128/290, 287, 290 R, 128/290 W

[56] References Cited

U.S. PATENT DOCUMENTS

| Re. 26,939 | 8/1970 | Hervey et al. | 128/284 |
|---|---|---|---|
| 811,704 | 2/1906 | Dix | 128/290 R |
| 2,548,341 | 4/1951 | Bricmont | 128/290 R |
| 2,643,656 | 6/1953 | Atkinson | 128/290 R |
| 2,705,497 | 4/1955 | Johnson et al. | 128/290 W |
| 3,036,573 | 5/1962 | Voigtman et al. | 128/290 R |
| 3,088,463 | 5/1963 | Harmon | 128/290 W |
| 3,095,878 | 7/1963 | Bassett | 128/290 W |
| 3,294,091 | 12/1966 | Morse | 128/290 R |
| 3,308,826 | 3/1967 | Blake | 128/290 W |
| 3,395,708 | 8/1968 | Hervey et al. | 128/290 R |
| 3,542,028 | 11/1970 | Beebe et al. | 128/290 R |
| 3,666,611 | 5/1972 | Joa | 428/78 |
| 3,809,089 | 5/1974 | Hedstrom et al. | 128/287 |
| 3,929,135 | 12/1975 | Thompson | 128/156 |
| 4,047,531 | 9/1977 | Karami | 128/290 R |
| 4,057,061 | 11/1977 | Ishikawa et al. | 128/290 R |
| 4,077,410 | 3/1978 | Butterworth et al. | 128/287 |

*Primary Examiner*—Robert W. Michell
*Assistant Examiner*—C. W. Shedd
*Attorney, Agent, or Firm*—E. Kelly Linman; John V. Gorman; Richard C. Witte

[57] ABSTRACT

A low-density disposable diaper is provided with an absorbent pad comprised of an airlaid mat of relatively stiff, high yield wood pulp fibers having relatively little cohesive strength in airlaid form or a similar low-strength absorbent material preferably encapsulated by an envelope of wet strength tissue paper. The absorbent pad is preferably enclosed between a liquid-retaining backsheet and a liquid-pervious topsheet secured in superposed relation to the liquid-retaining backsheet. A wet strength tissue ply having a maximum stretch characteristic of about thirty percent, as measured at the point of rupture, is preferably located in a plane approximately midway between the outermost tissue plies which encapsulate the low strength absorbent media. The low stretch, wet strength tissue ply imparts unexpected improvements in pad integrity to the structure in use, thereby facilitating maximum utilization of the greater void volume inherent in such low density structures for more efficient absorption and retention of body exudates.

8 Claims, 4 Drawing Figures

LOW-DENSITY DISPOSABLE ABSORBENT BANDAGE HAVING LOW STRETCH, WET STRENGTH CENTER PLY TO PROVIDE IMPROVED PAD INTEGRITY IN USE

BACKGROUND OF THE INVENTION

The present invention relates generally to disposable absorbent bandages, particularly to disposable diapers, and, more particularly, to a new and improved disposable absorbent diaper pad construction exhibiting low wet density and improved pad integrity in use.

In recent years, improvements in disposable diapers have revolutionized the diapering of infants. As the term "disposable" implies, these diapers are designed to be discarded after single use. Disposable diapers generally consist of an absorbent pad, a pad-covering topsheet which contacts the infant, and a liquid-impervious backsheet for containing liquid wastes within the absorbent pad. U.S. Pat. No. Re. 26,151 which issued to Duncan et al. on Jan. 31, 1967 and which is hereby incorporated herein by reference is representative of such prior art disposable diaper structures.

Various materials have been employed as the absorbent media in such disposable absorbent structures. When plies of creped cellulose wadding are employed as the absorbent media there is little or no need for enclosing the absorbent media within an envelope of wet strength tissue, since the creped cellulose wadding generally has sufficient strength to provide satisfactory in use pad integrity. When a low-strength material such as airlaid wood pulp fluff, commonly referred to as airfelt, is employed as the absorbent media, a strength-imparting envelope is generally necessary not only to provide satisfactory in use pad integrity, but also to avoid the dusting and linting problems commonly associated with such low-strength absorbent materials both during manufacture and in use. Failure to provide sufficient in use pad integrity in a disposable diaper adversely affects both its absorbency and its containment characteristics.

For absorbent pads comprised of conventional chemically processed wood pulp fibers which have at least some degree of cohesive strength in airlaid form it has been the practice to employ a pair of wet strength tissue plies to encapsulate the absorbent media to impart at least an adequate degree of in use pad integrity. U.S. Pat. No. 3,952,745 issued to Duncan on Apr. 27, 1976, said patent being hereby incorporated herein by reference, is representative of such structures. The lack of pad integrity in the absorbent fibrous media reaches critical proportions, however, when relatively stiff high yield wood pulp fibers, such as thermomechanical wood pulp fibers, which have very little cohesive strength in airlaid form are utilized as the absorbent medium. As utilized herein, high yield wood pulp fibers are considered to be those wherein the bulk of the lignin is not removed during processing. Thus, a much greater proportion of the tree from which the fibers are obtained is converted into fibers.

By way of contrast, conventional chemically processed wood pulp fibers are considered to be those wherein the lignin is substantially removed during processing. High yield fibers are typically non-collapsed, stiffer, and more resilient than the collapsed ribbon-like chemically processed fibers. Accordingly, there is less interentanglement of the high yield fibers with one another and consequently less cohesive strength in airfelts produced therefrom. Nonetheless, it is extremely desirable to utilize such fibers in disposable absorbent products, not only from the standpoint of more efficient utilization of natural resources due to reduced waste in converting the fibers, but also from the standpoint of reduced fiber utilization for an equivalent absorptive capacity. The relatively stiff and springy nature of high yield fibers provides an airfelt pad which exhibits a lower wet density in use than a pad formed from conventional chemically processed wood pulp fibers. Consequently, for comparable quantities of fibers, high yield wood pulp fiber pads exhibit greater void volume in use, and consequently greater absorptive capacity.

To date, the difficulty experienced with such pads, even when encapsulated in an envelope of wet strength tissue paper, has been that the greater void volume could not be effectively utilized to absorb and retain body exudates due to a lack of in use pad integrity. The actions of the wearer typically cause such pads to disintegrate, thereby producing a wet strength tissue envelope containing a mass of loose, unbonded fibers which are free to shift about the interior of the envelope. Such structures exhibit extremely low void volumes in use and are clearly ineffectual in the absorption and retention of body exudates.

Various means to strengthen or reinforce airfelt pad structures are well known in the art. Typical approaches to this problem are the addition of adhesive coated scrims internal to the pad and the application of reinforcing resins or foam forming agents to the exposed fibrous surfaces of the pad. However, such prior art solutions to the problem of in use pad integrity in absorbent fibrous structures are relatively high in cost, thereby adversely affecting the overall economy of use of such disposable absorbent structures. Furthermore, such solutions are often too complex to reliably execute, and in general cannot readily be carried out without major design changes in the disposable absorbent structure per se.

OBJECTS OF THE INVENTION

In view of the disadvantages and shortcomings of prior art low-density disposable absorbent bandages, it is an object of the present invention to provide a low-density disposable absorbent bandage comprised primarily of relatively stiff high yield fibers having little cohesive strength in airlaid form, said bandage exhibiting an absorptive capacity comparable to that of prior art structures of greater basis weight due to its lower wet density in use, yet having sufficient in use pad integrity to permit effective utilization of the greater void volume inherent in such a structure.

It is another object of the present invention to provide a simple, low cost means of imparting adequate in use pad integrity to a low-density disposable absorbent bandage comprised primarily of relatively stiff high yield wood pulp fibers.

A further object of the present invention is to provide a practical, low-density disposable absorbent bandage exhibiting an absorptive capacity substantially equivalent to that of prior art structures of higher basis weight and greater wet density in use, thereby reducing the total quantity of fibers required to manufacture such structures without any sacrifice in their absorptive capacity.

Still another object of the present invention is the provision of a strong, low-density disposable absorbent bandage employing primarily high yield fibers as the absorbent media to permit more effective utilization of natural resources.

SUMMARY OF THE INVENTION

In a particularly preferred embodiment, a low-density disposable absorbent bandage having a moisture-pervious topsheet for contacting the wearer's body, a moisture absorbent pad for absorbing and retaining body exudates and a moisture-impervious backsheet opposite the wearer contacting surface secured in superposed relation to one another is provided. The moisture absorbent pad, which has a maximum wet density of about 0.10 grams per cubic centimeter, as measured under an applied load of 80 grams per square inch, i.e., 12 grams per square centimeter, is preferably comprised primarily of relatively stiff, high yield wood pulp fibers constrained within an evelope of wet strength tissue paper. At least one ply of wet strength tissue paper having a maximum dry stretch characteristic of about 30 percent, as measured at the point of rupture, is provided in a plane approximately midway between the outermost surfaces of said wet strength tissue envelope and surrounded on both sides by said high yield wood pulp fibers to impart improved in use integrity to said absorbent pad. The resulting disposable absorbent structure exhibits an in use pad integrity and an absorptive capacity comparable to those of more dense prior art structures employing the more expensive conventional chemically processed wood pulp fibers without the use of a limited stretch wet strength tissue ply intermediate the envelope tissue plies, yet utilizes a lesser quantity of fibers.

BRIEF DESCRIPTION OF THE DRAWINGS

While the specification concludes with claims particularly pointing out and distinctly claiming the present invention, it is believed that the invention will be better understood by reference to the following explanation and accompanying drawings in which:

DESCRIPTION OF THE PREFERRED EMBODIMENTS

Figure 1:
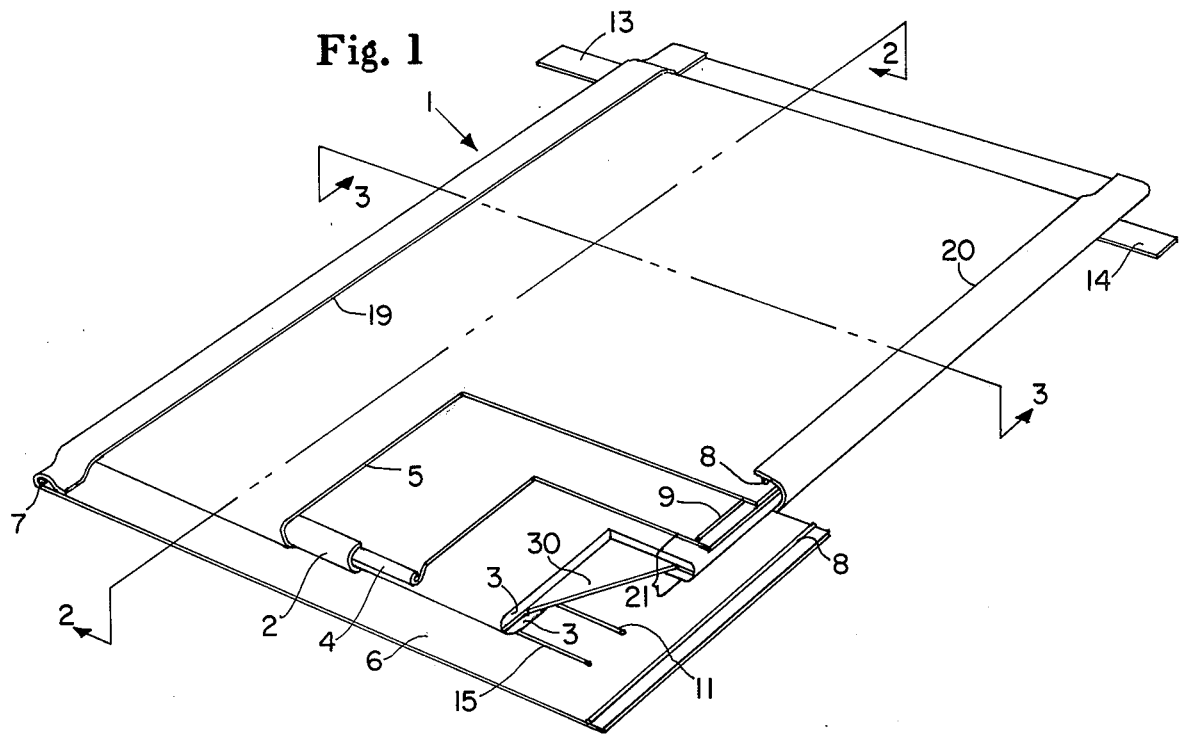
FIG. 1 is a perspective view of a preferred embodiment of a disposable diaper of the present invention with one corner section broken out to illustrate the relationship of the various structural elements.

FIG. 1 is illustrative of a preferred embodiment of a disposable diaper of the present invention. Typically, a disposable diaper 1 of the present invention comprises a liquid-impervious backsheet 6, a liquid absorbent pad 21, and a moisture-pervious body contacting topsheet 5. The backsheet 6 may be of plastic, treated paper, or the like and will typically wrap over the absorbent pad 21 and topsheet 5 at the edges to provide side flaps 19 and 20 which serve to improve the containment characteristics of the diaper, as taught by U.S. Pat. No. Re. 26,151 which issued to Duncan et al. on Jan. 31, 1967, said patent being incorporated herein by reference. In a particularly preferred embodiment of the present invention, the airlaid fibrous absorbent media 3 contained in the liquid absorbent pad 21 is comprised primarily of relatively stiff, high yield wood pulp fibers, such as thermomechanical pulp fibers, which have relatively little cohesive strength in airlaid form. This is believed to be due primarily to the stiffness and lack of interentanglement of such fibers when formed into an airlaid web. If desired, a small portion of conventional chemically processed wood pulp fibers may be blended in to enhance the cohesiveness of an airlaid web utilized in the practice of the present invention. It should be noted, however, that the addition of conventional chemically processed wood pulp fibers in the airlaid web tends to increase the overall wet density of the web in use, thereby decreasing its void volume and consequently detracting from its absorptive capacity. Furthermore, it increases the cost of the resultant disposable absorbent product due to the greater cost of the chemically processed wood pulp fibers.

Absorbent pads employing airlaid fibrous webs to which the practice of the present invention has particular utility generally exhibit a maximum wet density of less than about 0.10 grams per cubic centimeter, as measured under a load of 80 grams per square inch i.e., 12 grams per square centimeter.

Wet densities of the absorbent pad structures 21 referenced throughout the specification and claims were determined utilizing 4 inch by 4 inch absorbent pad samples, i.e., envelope tissue plies 2, 4, absorbent media 3 and tissue ply 30 where utilized. The absorbent pad samples were initially calendered to a dry density of 0.10 grams per cubic centimeter, as measured under a load of 80 grams per square inch i.e., 12 grams per square centimeter. The samples were wetted with a quantity of one percent saline simulated urine solution having its surface tension adjusted to 45 dynes per centimeter. The quantity of solution applied amounted to three times the dry weight of the absorbent pad sample. The wetted samples were then placed in a Model No. 13 Ames Dial Comparator employing an Ames No. 482 Gauge, such as is available from B. C. Ames Company of Waltham, Mass., and a load of 0.50 pounds per square inch was applied to the sample via the 2.0 square inch foot of the Comparator to simulate the loads typically applied by an infant sitting in a wetted diaper. The 0.50 pounds per square inch loading was applied sequentially in approximately 40 grams per square inch, i.e., 6 grams per square centimeter, pressure increments awaiting a stable or equilibrium condition on the Dial Comparator prior to applying the next pressure increment until the target loading was obtained and the Dial Comparator had stabilized. The 0.50 pounds per square inch applied load was then released for a period of approximately one minute to permit the pad sample to seek its own equilibrium, and a load of 80 grams per square inch, i.e., 12 grams per square centimeter, was thereafter applied while the wet caliper measurement was taken. Wet density of the sample was calculated by the following equation:

$$\text{Wet Density} = \frac{\left[\begin{array}{c}\text{Dry Weight of 4}'' \times 4'' \\ \text{Absorbent Pad Sample}\end{array}\right]}{\left[\begin{array}{c}\text{Area of} \\ 4'' \times 4'' \text{ Pad} \\ \text{Sample}\end{array}\right] \times \left[\begin{array}{c}\text{Wet Caliper} \\ \text{of Pad} \\ \text{Sample}\end{array}\right]}$$

By way of contrast, prior art absorbent pad structures utilizing primarily conventional chemically processed wood pulp fibers typically exhibit wet densities on the order of about 0.12 grams per cubic centimeter or greater when measured under similar conditions. As is well known in the disposable absorbent bandage art, absorbent structures exhibiting low wet densities are generally desirable since they exhibit greater void volumes in use, and consequently greater absorption and retention capacity for a given weight of fibers.

Figure 2:
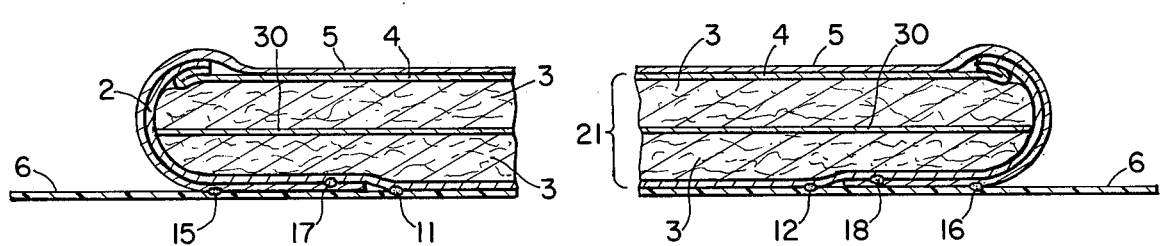
FIG. 2 is an enlarged cross-sectional view of the disposable diaper illustrated in FIG. 1 taken along Section Line 2—2 of FIG. 1.
Figure 3:
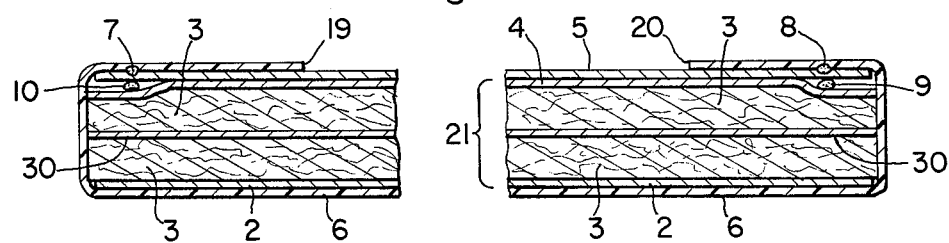
FIG. 3 is an enlarged cross-sectional view of the disposable diaper illustrated in FIG. 1 taken along Section Line 3—3 of FIG. 1.

The manner in which the various elements are assembled is more clearly illustrated in FIGS. 2 and 3. As can be seen in FIG. 2, the topsheet 5 is folded about the absorbent pad 21 at the ends or waistband portions of the diaper. The overlapping portions of the topsheet 5 are secured directly to the backsheet 6 by means of beads of adhesive 15 and 16 extending essentially across the entire width of the absorbent pad 21. The absorbent media 3 and a limited stretch, wet strength tissue ply 30 are contained between layers of wet strength tissue paper 2 and 4. The end portions of the uppermost layer of wet strength tissue paper 4 are folded back upon themselves, while the end portions of the lowermost layer of wet strength tissue paper 2 are folded back over the end portions of the uppermost layer of wet strength tissue paper to form an envelope about the absorbent media 3 and tissue ply 30. The absorbent pad 21 is thus constrained within an outer envelope formed by the topsheet 5 and the moisture-impervious backsheet 6. The absorbent pad 21 is preferably secured to the overlapping portions of the topsheet 5 by means of beads of adhesive 17 and 18 which extend essentially across the entire width of the absorbent pad. Beads of adhesive 11 and 12 which also extend essentially across the entire width of the absorbent pad are preferably utilized to secure the lowermost layer of wet strength tissue paper 2 directly to the innermost surface of the moisture-impervious backsheet 6.

Referring now to FIG. 3, it can be seen that the liquid absorbent pad 21 is constrained along the edge portions of the diaper within the envelope formed by the liquid-pervious topsheet 5 and the overlapping edge portions of the moisture-impervious backsheet 6 which are joined together along the edge portions of the diaper by means of beads of adhesive 7 and 8 which preferably extend the entire length of the backsheet. It should be noted that the inner overlapping edge portions 19 and 20 of the moisture-impervious backsheet 6 are not secured directly to the topsheet in order to provide a gasketing action and hence better containment of exuded body fluids in accordance with the teachings of the aforementioned patent to Duncan et al. The uppermost surface of wet strength tissue layer 4 is preferably secured to the lowermost surface of the liquid-pervious topsheet 5 by means of beads of adhesive 9 and 10 which extend the entire length of the absorbent pad 21. Due to the liquid-pervious nature of the topsheet 5 utilized in one preferred embodiment of the present invention, beads of adhesive 9 and 10 are normally provided simply by migration of a portion of the adhesive utilized to form beads 7 and 8 directly through the liquid-pervious topsheet while the adhesive is in a liquid state. In yet another preferred embodiment of the present invention a liquid-pervious top sheet 5 comprised of liquid-impervious material provided with tapered capillaries of critical diameters and tapers, each capillary having a base in the plane of the topsheet and an apex remote from the plane of the topsheet and in intimate contact with the absorbent pad 21, may be employed. U.S. Pat. No. 3,929,135 issued to Thompson on Dec. 30, 1975 and incorporated herein by reference is representative of such a topsheet. In the latter embodiment, beads of adhesive 9 and 10 are preferably applied directly.

A disposable diaper of the present invention is preferably secured in place about the waist of the wearer by means of pressure-sensitive adhesive tape fasteners 13 and 14 which are well known in the disposable diapers art.

As is shown in FIGS. 1, 2 and 3, the low strength absorbent media of high yield wood pulp fibers 3 is preferably enveloped between a pair of tissue sheets 2, 4 having at least moderate wet strength. As with structures employing conventional chemically processed wood pulp fibers, the wet strength tissue sheets 2, 4 are utilized to maximize in use pad integrity and to prevent dusting or linting of the absorbent fibers 3 in the pad through the body contacting topsheet 5. In a particularly preferred embodiment of the present invention, a wet strength tissue ply 30 having a maximum dry stretch characteristic of approximately 30 percent, as measured at the point of ply rupture, is provided within the wet strength tissue envelope. preferably in a plane about midway between the wet strength tissue plies 2, 4 and surrounded on both sides by absorbent airlaid high yield wood pulp fibers 3. While it is not essential to the practice of the present invention that the tissue ply 30 divide the total thickness of airfelt contained within the envelope tissues 2, 4 in a 50:50 ratio, applicant has learned that benefits provided by the present invention are greatest when the ratio of the thickness of one layer of airfelt relative to the other does not exceed approximately 70:30.

While the provision of one or more tissue layers at various locations within an absorbent airfelt medium are known to be old in the art, applicant has discovered that provision of a wet strength tissue layer having a maximum dry stretch characteristic of approximately 30 percent produces an unexpected increase in the amount of stretch an absorbent pad 21 comprised primarily of airlaid wood pulp fibers can undergo before the fibrous media begins to crack or separate when the absorbent pad structure 21 is subjected to tensile loading. This unexpected improvement, when applied to high yield wood pulp fibers, provides a highly absorptive, low-density disposable absorbent bandage exhibiting in use pad integrity comparable to that of prior art disposable absorbent bandages employing conventional chemically processed wood pulp fibers in airlaid form, but without a centrally-located, limited stretch, wet strength tissue ply 30. It is particularly noteworthy that a limited stretch, wet strength tissue ply 30 of the present invention need only be interposed intermediate the outermost wet strength tissue plies 2, 4 forming the envelope which encapsulates the absorbent fibrous media 3, but not necessarily secured thereto.

Although the limited stretch, wet strength tissue ply 30 may, if desired, be secured to either of the outermost plies 2, 4 or both, applicant has found it advantageous for the tissue ply 30 to remain unsecured to either the absorbent fibrous media 3 on either side thereof or the outermost tissue plies 2, 4. This approach has proven beneficial in two regards. First, this minimizes the material cost of the additional tissue ply 30 since it may be smaller than either of the outermost tissue plies 2, 4. Secondly, leaving the intermediate tissue ply 30 unsecured in the manner illustrated in FIGS. 1 to 3 minimizes any adverse effect on flushability of the absorbent fibrous media 3 upon disposal in a water closet. To wit, the present invention may readily be practiced in a disposable absorbent diaper structure such as that disclosed in U.S. Pat. No. 3,952,745 issued to Duncan on Apr. 27, 1976. When a disposable diaper 1 of the present invention has become soiled, the moisture-impervious backsheet 6 may be stripped from the remainder of the diaper to permit disposal of the soiled portion of the diaper in a conventional toilet. This is preferably accomplished by severing beads of adhesive 15 and 16 between the backsheet and topsheet along the end portions of the diaper. Beads of adhesive 11 and 12 which secure the lowermost layer of wet strength tissue 2 directly to the moisture-impervious backsheet 6 are not severed, however, by the aforementioned stripping action. Beads of adhesive 11 and 12 are preferably sufficiently strong to securely bond the wet strength tissue layer 2 to the backsheet so that the stripping action applied to the backsheet will cause the lowermost panel of wet strength tissue to rupture outside the beads of adhesive and thereby cause that portion of the lowermost layer of wet strength tissue paper located intermediate the adhesive glue beads 11 and 12 to remain in adherent contact with the moisture-impervious backsheet 6 when the backsheet is removed from the remainder of the structure. Thus, a large panel of wet strength tissue envelope utilized to impart strength to the liquid absorbent media 3 in use is removed to permit rapid hydraulic erosion of that portion of the absorbent media remaining within the envelope adjacent the lowermost surface of intermediate tissue ply 30 upon rinsing of the soiled portions of the diaper in a toilet bowel. Because the intermediate tissue ply 30 is unsecured to either tissue ply 2 or 4 in a preferred embodiment of the present invention, it may be readily removed either manually or by the action of the flushing toilet, thereby exposing that portion of the fibrous absorbent media 3 adjacent the uppermost surface of the tissue ply 30 to hydraulic erosion.

To illustrate the unexpected benefits provided by the present invention, a number of sample diaper pads were prepared generally in accordance with the teachings of U.S. Pat. No. 3,952,745 employing a wet strength tissue envelope, i.e. plies 2, 4 comprised of tissue paper having a basis weight of about 12 pounds per 3,000 square feet, a dry MD stretch characteristic of about 16 percent, as measured at the point of rupture, a dry CD stretch characteristic of about 4 percent, a dry MD tensile strength of approximately 680 grams per inch, i.e., 268 grams per centimeter, a dry CD tensile strength of approximately 430 grams per inch, i.e., 169 grams per centimeter, a wet MD tensile strength of approximately 155 grams per inch, i.e., 61 grams per centimeter, and a wet CD tensile strength of approximately 100 grams per inch, i.e., 39 grams per centimeter. The diaper pad samples were prepared so that the machine direction of the tissue plies 2, 4 was aligned parallel to the waistband portions of the diaper, i.e., parallel to the adhesive beads 11 and 15 illustrated in FIGS. 1 and 2. This is generally done to align the direction of greatest strength of the tissue plies 2, 4 with the direction of greatest tensile loading in use. The prior art diaper pads 21 of Example 1 were prepared utilizing conventional airlaid chemically processed wood pulp fibers 3 and exhibited a basis weight of approximately 0.033 grams per square centimeter.

To establish the integrity of the prior art diaper pads 21 of Example 1, the pads, i.e., tissue plies 2, 4 and airfelt 3, were calendered so that the absorbent pad samples exhibited an initial dry density of approximately 0.10 grams per cubic centimeter, as measured under a load of 80 grams per square inch, i.e., 39 grams per centimeter. Pad samples measuring 3 inches in the cross-machine direction of the tissue plies by 6 inches in the machine direction of the tissue plies were cut. The samples were wetted with a quantity of 1 percent saline simulated urine solution having a surface tension of 45 dynes per centimeter amounting to approximately 3 times the dry weight of the pad sample. Half of the solution was applied to each side of the sample to promote uniform wetting. The pad samples were then subjected to a compressive loading of approximately 1 pound per square inch for a period of approximately 10 minutes to allow for moisture equilibration. The wetted samples were thereafter mounted in a Model TM Instron tensile tester, as manufactured by Instron Engineering Corporation of Canton, Mass., such that their 6 inch dimension, i.e., the machine direction of the tissue plies 2, 4 was parallel to the direction of movement of the tensile tester jaws. An initial jaw spacing of 4 inches was employed, and the samples were mounted such that each jaw gripped a 1 inch long segment of the pad. A light source was placed behind the pad sample for visual clarity in observing the behavior of the airfelt during the tensile testing carried out on the Instron. The samples were subjected to tensile loading at a jaw speed of approximately 0.10 inches per minute until visible separation or cracking of the airfelt was observed. The stretch level of the pad sample at the point of airfelt separation or cracking was recorded.

Utilizing the aforementioned test procedure it was determined that the prior art diaper pads of Example 1 underwent a stretch level of approximately 11 percent at the point of airfelt cracking.

The diaper pads of Example 2 were constructed in essentially the same manner as the diaper pads of Example 1, with the exception that airlaid thermomechanical wood pulp fibers were substituted for the chemically processed wood pulp fibers of Example 1. The diaper pads 21 of Example 2 exhibited a basis weight of approximately 0.035 grams per square centimeter. The diaper pads of Example 2 underwent a stretch level of approximately 4.6 percent at the point of airfelt cracking. Experience has shown that diapers exhibiting such a low stretch level at the point of airfelt cracking do not have sufficient in use integrity to facilitate effective use as a disposable diaper.

To isolate the effect of adding a centrally-located, limited stretch, wet strength tissue ply 30 to the absorbent pads 21 of Example 2, the diaper pads of Example 3 were constructed in basically the same manner as the diapers of Example 2, with the exception that an intermediate tissue ply 30 was provided approximately midway between the two outermost tissue plies 2, 4. The intermediate tissue ply was unsecured to either the absorbent media 3 or the outermost wet strength tissue plies 2, 4. The wet strength tissue ply 30 which was generally similar to the outermost wet strength tissue plies 2, 4 exhibited a basis weight of approximately 12 pounds per 3,000 square feet, as measured in an uncreped condition, and a wet MD tensile strength of at least about 100 grams per inch, i.e., 39 grams per centimeter. The machine direction of the ply 30 was oriented to coincide with the machine direction of the tissues plies 2, 4, i.e., parallel to adhesive beads 11 and 15 illustrated in FIGS. 1 and 2 and parallel to the direction of jaw movement on the tensile tester. This particular orientation of the tissue ply 30, although not critical to the practice of the present invention, is generally preferred since it aligns the desired dry stretch characteristic and the greatest strength of the ply with the direction of greatest tensile loading in use, thereby maximizing the improvement in pad integrity provided by the present invention. The amount of crepe imparted to the center ply 30 was intentionally varied so that the dry stretch characteristic exhibited by the center ply, as measured at the point of ply rupture, varied between about 16 percent and about 98 percent for the range of sample pads of Example 3 subjected to stretch testing. The basis weight of the diaper pads of Example 3 amounted to at least approximately 0.036 grams per square centimeter.

Figure 4:
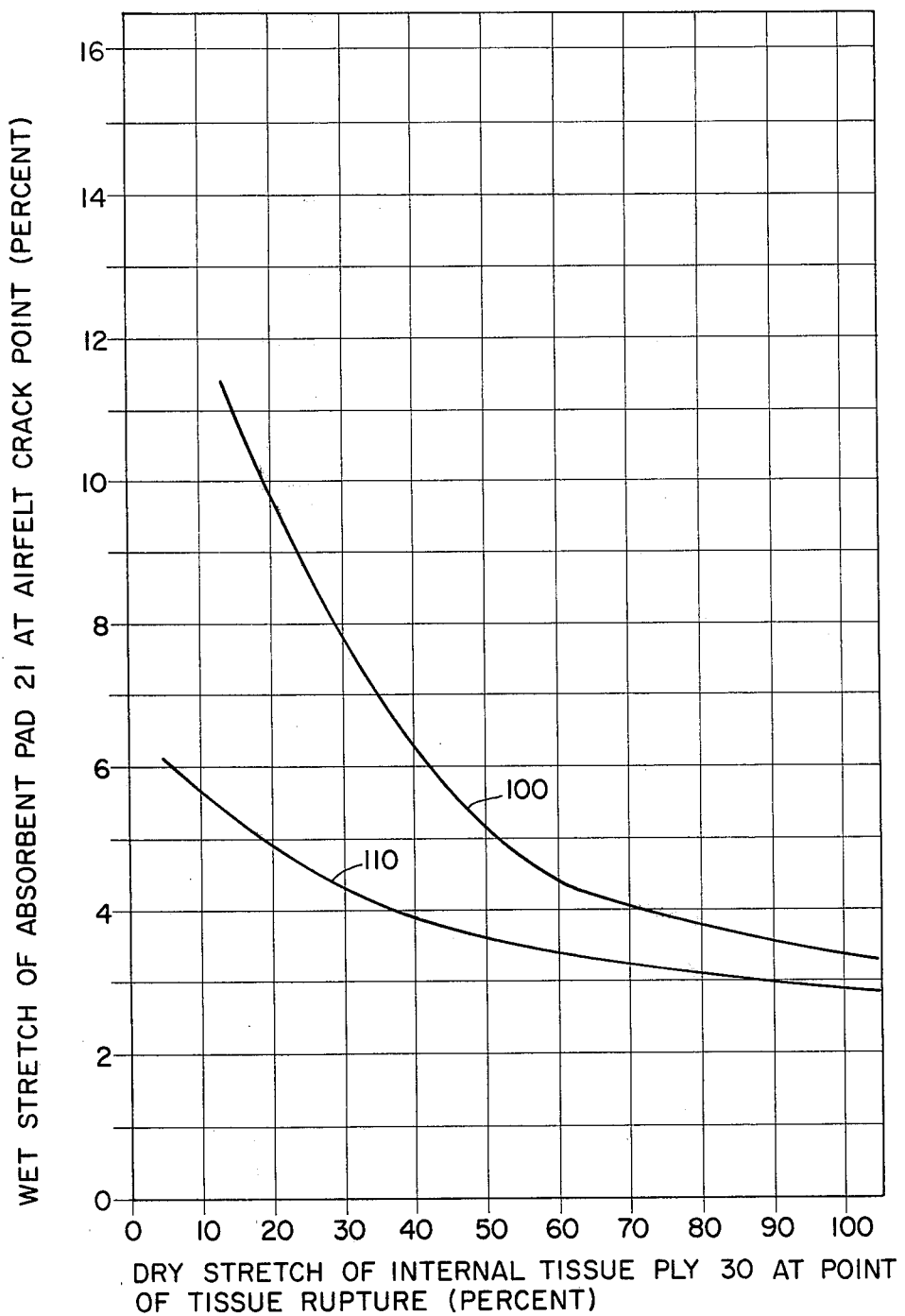
FIG. 4 is a graph illustrating the effects of wet strength and degree of dry stretch of the internally located tissue ply on pad integrity.

The results of the stretch testing conducted on the pad samples of Example 3 is graphically illustrated by line 100 in FIG. 4, which is a graph comparing the percentage wet stretch of the airfelt at the point of cracking against the percentage dry stretch of the centrally-located tissue ply 30, as measured at the point of ply rupture.

As is apparent from line 100 in FIG. 4, when the dry stretch characteristic of the centrally-located tissue ply 30 is about 30 percent or less, the wet stretch characteristic of the absorbent pad samples of Example 3 employing airlaid thermomechanical pulp fibers approaches that of the prior art chemically processed wood pulp diaper pads of Example 1. Furthermore, the wet stretch characteristic of said diaper pads is approximately double that of the diaper pads of Example 2 which do not incorporate a centrally-located tissue ply 30. It should be noted, however, that as the dry stretch characteristic of the centrally-located tissue ply 30 increases to about 60 percent or more, the wet stretch characteristic of the pad sample as measured at the point of airfelt cracking approaches parity with the pad samples of Example 2. Thus, in a preferred embodiment of the present invention, the wet strength tissue ply 30 exhibits a dry stretch characteristic, as measured at the point of ply rupture, of about 30 percent or less.

To isolate the effect of wet strength level on the tissue ply 30, diaper pads of Example 4 were constructed in essentially the same manner and at substantially the same basis weights as those of Example 3, but the minimum wet MD tensile strength of the tissue ply 30 amounted to only about 25 grams per inch, i.e., 10 grams per centimeter. The amount of crepe imparted to the center ply 30 was varied so that the dry stretch exhibited by the center ply, as measured at the point of ply rupture, varied between about 11 percent and about 93 percent for the range of pad samples of Example 4 subjected to testing.

The results of the stretch testing conducted on the pad samples of Example 4 is graphically illustrated by line 110 in FIG. 4. Even at dry stretch characteristics of 30 percent or less in the tissue ply 30, the wet stretch characteristics exhibited by the pad samples of Example 4 at the point of airfelt cracking were only slightly better than those of the unreinforced pad samples of Example 2. Thus, in a preferred embodiment of the present invention, a minimum wet tensile strength of at least about 100 grams per inch, i.e., 39 grams per centimeter, as measured in a direction parallel to the desired dry stretch characteristic of the ply, has been found desirable.

In order to assess the meaningfulness of the quantitative stretch data generated with respect to Examples 1–3 above, an in use diaper test was devised. The test procedure involved placing disposable diaper samples on active babies ranging in age between about 12 and about 24 months, initially introducing 50 milliliters of 1 percent saline simulated urine solution over a period of 10 seconds by means of a tube designed to discharge the solution in the area of the diaper wherein urine is normally discharged by the baby. The baby was thereafter allowed to resume its normal activities for a period of about 10 minutes, at which time an additional 50 milliliters of simulated urine solution was introduced in the same manner. The baby was then allowed to resume its activities for a period of 20 minutes, at which time the diaper was removed and visually inspected for airfelt separation or cracking. The results of the visual examination were broadly grouped into two catagories:

(a) those diaper samples wherein the maximum dimension of any airfelt separation observed was one inch or less; and
(b) those diaper samples wherein the maximum dimension of any airfelt separation was greater than about one inch.

When the maximum dimension of airfelt separation exceeds about one inch, experience has demonstrated that the continuity of the absorbent core has been significantly impaired, and the absorptive capacity of the diaper is reduced.

To isolate the effect of wearing time on pad integrity the aforementioned test was repeated, increasing the wearing time after the second wetting from 20 minutes to 50 minutes. A third test was also conducted, this time increasing the wearing time after the second wetting from 20 minutes to 80 minutes.

The diaper pads 21 of Examples 1 and 2 were of the same construction described earlier herein. The diaper structures in which the pads were incorporated were basically in accordance with the teachings of U.S. Pat. No. 3,952,745, but employing a tapered capillary topsheet of the type generally disclosed in U.S. Pat. No. 3,929,135, said patents being incorporated herein by reference. One set of diaper samples made in accordance with Example 3 employed a centrally-located tissue ply 30 having a maximum dry MD stretch characteristic, as measured at the point of ply rupture, of approximately 16 percent and a wet MD tensile strength of approximately 155 grams per inch, i.e., 61 grams per centimeter. The absorbent pads 21 of this particular set of diapers exhibited a basis weight of approximately 0.036 grams per square centimeter and a wet density of approximately 0.090 grams per cubic centimeter, as measured under a load of 80 grams per square inch, i.e., 12 grams per square centimeter. The other set of diaper samples made in accordance with Example 3 employed a centrally-located tissue ply 30 having a maximum dry MD stretch characteristic of approximately 98 percent and a wet MD tensile strength of approximately 110 grams per inch, i.e., 43 grams per centimeter. The absorbent pads 21 of the latter set of diapers exhibited a basis weight of approximately 0.040 grams per square centimeter and a wet density of approximately 0.095 grams per cubic centimeter, as measured under a load of 80 grams per square inch, i.e., 12 grams per square centimeter.

The results of the foregoing tests are set forth below in Table I:

As should be apparent from an analysis of the data set forth in Table I, the Example 2 diapers employing thermomechanical wood pulp fibers without any type of reinforcing ply were extremely prone to pad integrity problems at all wearing times. The Example 3 diapers employing a centrally-located tissue ply having a dry MD stretch characteristic of approximately 98 percent exhibited improved integrity over the diapers of Exam-

TABLE I

| Test Results | Diaper Pad Construction | | | |
|---|---|---|---|---|
| | Example 1 Diapers: Prior Art Chemically Processed Wood Pulp Fibers; No Centrally-located Tissue Ply | Example 2 Diapers: Thermomechanical Wood Pulp Fibers; No Centrally-located Tissue Ply | Example 3 Diapers: Thermomechanical Wood Pulp Fibers; Centrally-located, Wet Strength Tissue Ply Having 16% Dry Stretch Characteristic | Example 3 Diapers: Thermomechanical Wood Pulp Fibers; Centrally-located, Wet Strength Tissue Ply Having 98% Dry Stretch Characteristic |
| $\dfrac{\text{No. of diaper samples exhibiting no airfelt cracking in excess of 1'' after 30 mins. total wearing time}}{\text{No. of diaper samples tested}}$ | $\dfrac{9}{11}$ | $\dfrac{3}{10}$ | $\dfrac{9}{9}$ | $\dfrac{7}{11}$ |
| $\dfrac{\text{No. of diaper samples exhibiting airfelt cracking in excess of 1'' after 30 mins. total wearing time}}{\text{No. of diaper samples tested}}$ | $\dfrac{2}{11}$ | $\dfrac{7}{10}$ | $\dfrac{0}{9}$ | $\dfrac{4}{11}$ |
| $\dfrac{\text{No. of diaper samples exhibiting no airfelt cracking in excess of 1'' after 60 mins. total wearing time}}{\text{No. of diaper samples tested}}$ | $\dfrac{7}{10}$ | $\dfrac{2}{10}$ | $\dfrac{5}{9}$ | $\dfrac{4}{9}$ |
| $\dfrac{\text{No. of diaper samples exhibiting airfelt cracking in excess of 1'' after 60 mins. total wearing time}}{\text{No. of diaper samples tested}}$ | $\dfrac{3}{10}$ | $\dfrac{8}{10}$ | $\dfrac{4}{9}$ | $\dfrac{5}{9}$ |
| $\dfrac{\text{No. of diaper samples exhibiting no airfelt cracking in excess of 1'' after 90 mins. total wearing time}}{\text{No. of diaper samples tested}}$ | $\dfrac{6}{8}$ | $\dfrac{0}{9}$ | $\dfrac{5}{9}$ | $\dfrac{0}{8}$ |
| $\dfrac{\text{No. of diaper samples exhibiting airfelt cracking in excess of 1'' after 90 mins. total wearing time}}{\text{No. of diaper samples tested}}$ | $\dfrac{2}{8}$ | $\dfrac{9}{9}$ | $\dfrac{4}{9}$ | $\dfrac{8}{8}$ | ple 2 at wearing times of 30 and 60 minutes, but no difference at 90 minutes. The Example 3 diapers employing a centrally-located tissue ply having a dry MD stretch characteristic of approximately 16 percent and which represent a preferred embodiment of the present invention exhibited no severe pad integrity problems after 30 minutes wearing time, and performance approaching parity with the prior art diapers of Example 1 at wearing times of 60 and 90 minutes. Thus the quantitative data described in connection with FIG. 4 correlates well with the aforementioned in use observations.

While the present invention has been described in particular detail with reference to several preferred disposable diaper embodiments, it is not intended to hereby limit to the particular embodiments shown and described. Depending upon the total thickness of the absorbent media in the particular application, the present invention may be extended to multiple reinforcing plies, the plies being separated from one another by a layer of airfelt or other low strength absorbent media. Furthermore, the direction of maximum dry stretch of the various plies may be staggered with respect to one another to improve the overall integrity of the structure regardless of the direction in which tensile loading is applied. Many other variations of the present invention will be apparent to those skilled in the art.

What is claimed is:

1. In a disposable absorbent bandage comprising a moisture-pervious topsheet for contacting the wearer's body, a moisture-absorbent pad for absorbing and retaining body exudates, and a moisture-impervious backsheet opposite the wearer contacting surface secured in superposed relation to one another, the improvement wherein said moisture absorbent pad is comprised primarily of relatively stiff, airlaid, high yield, substantially non-delignified wood pulp fibers constrained within an envelope of wet strength tissue paper, said moisture absorbent pad including at least one ply of wet strength tissue paper having a maximum dry stretch characteristic of about 30 percent, as measured at the point of rupture, located in a plane intermediate the outermost surfaces of said wet strength tissue envelope and surrounded on both sides by said high yield wood pulp fibers, said moisture absorbent pad exhibiting a maximum wet density of approximately 0.10 grams per cubic centimeter, as measured at a one percent saline simulated urine loading amounting to about three times the weight of the absorbent pad sample under an applied load of 12 grams per square centimeter, said moisture absorbent pad exhibiting improved absorptive capacity and integrity in use.

2. The disposable absorbent bandage of claim 1, wherein said wet strength tissue ply located in a plane intermediate the outermost surfaces of said wet strength tissue envelope exhibits a wet tensile strength of at least about 39 grams per centimeter, as measured in a direction parallel to the direction of its maximum dry stretch characteristic.

3. The disposable absorbent bandage of claim 1, wherein said wet strength tissue ply located in a plane intermediate the outermost surfaces of said wet strength tissue envelope and surrounded on both sides by airlaid high yield wood pulp fibers divides the total thickness of said fibers within said envelope into two layers, the ratio of the thickness of one layer relative to the thickness of the other not exceeding about 70:30.

4. The disposable absorbent bandage of claim 3, wherein said wet strength tissue ply is located in a plane approximately midway between the outermost surfaces of said wet strength tissue envelope.

5. The disposable absorbent bandage of claim 1, comprising a disposable diaper wherein said wet strength tissue ply located in a plane intermediate the outermost surfaces of said wet strength tissue envelope is oriented so that its direction of maximum dry stretch coincides with the direction of maximum wet tensile strength of the wet strength tissue paper comprising said envelope, said direction of maximum wet tensile strength being aligned parallel to the waistband portions of said diaper.

6. The disposable absorbent bandage of claim 1, wherein said ply of wet strength tissue paper located in a plane intermediate the outermost surfaces of said wet strength tissue envelope and surrounded on both sides by said airlaid high yield wood pulp fibers is unsecured to said envelope.

7. The disposable absorbent bandage of claim 1, wherein said ply of wet strength tissue paper located in a plane intermediate the outermost surfaces of said wet strength tissue envelope and surrounded on both sides by said airlaid high yield wood pulp fibers is coextensive with the area occupied by said airlaid high yield wood pulp fibers, thereby dividing said airlaid fibers into two discrete layers.

8. The disposable absorbent bandage of claim 1, wherein said ply of wet strength tissue paper located in a plane intermediate the outermost surfaces of said wet strength tissue envelope is substantially impervious to the passage of said high yield wood pulp fibers from one surface thereof to the other.

* * * * *

UNITED STATES PATENT AND TRADEMARK OFFICE
CERTIFICATE OF CORRECTION

PATENT NO. : 4,327,729
DATED : May 4, 1982
INVENTOR(S) : LAWRENCE W. KING

It is certified that error appears in the above-identified patent and that said Letters Patent are hereby corrected as shown below:

Column 3, line 18, "evelope" should read -- envelope --.

Column 4, line 28, "inch" should read -- inch, --.

Column 4, line 38, "inch" should read -- inch, --.

Column 6, line 4, "top sheet" should read -- topsheet --.

Column 8, line 14, "39" should read -- 12 --.

Column 8, line 14, after "grams per", second occurrence, insert -- square --.

Column 9, line 8, "tissues" should read -- tissue --.

Signed and Sealed this

Tenth Day of August 1982

[SEAL]

Attest:

GERALD J. MOSSINGHOFF

Attesting Officer    Commissioner of Patents and Trademarks